(12) United States Patent
Schwartz et al.

(10) Patent No.: US 7,493,230 B2
(45) Date of Patent: Feb. 17, 2009

(54) METHOD AND APPARATUS FOR CUSTOMIZING INSOLES FOR FOOTWEAR

(75) Inventors: Evan Schwartz, New York, NY (US); Matthew Schwartz, New York, NY (US); Roberto Cahanap, Maywood, NJ (US); Larry Schwartz, Closter, NJ (US)

(73) Assignee: Aetrex Worldwide, Inc., Teaneck, NJ (US)

( * ) Notice: Subject to any disclaimer, the term of this patent is extended or adjusted under 35 U.S.C. 154(b) by 292 days.

(21) Appl. No.: 11/447,305

(22) Filed: Jun. 6, 2006

(65) Prior Publication Data

US 2007/0282562 A1    Dec. 6, 2007

(51) Int. Cl.
G01L 19/00 (2006.01)
G06F 15/00 (2006.01)

(52) U.S. Cl. ...................... 702/139; 702/155

(58) Field of Classification Search ............... 702/155, 702/167; 356/601; 382/100, 154, 165; 36/44; 705/26; 700/95
See application file for complete search history.

(56) References Cited

U.S. PATENT DOCUMENTS

| | | | |
|---|---|---|---|
| 88,494 A | 3/1869 | Lowrey | |
| 1,780,574 A | 11/1930 | Williams | |
| 2,200,849 A | 5/1940 | Margolin | |
| 2,776,500 A | 1/1957 | Gonsalves | |
| 2,853,805 A | 9/1958 | Dratman | |
| 2,917,844 A | 12/1959 | Scholl | |
| 2,928,193 A | 3/1960 | Kristan | |
| 3,143,812 A | 8/1964 | Bittner | |
| 3,195,244 A | 7/1965 | Whitcas | |
| 3,672,077 A | 6/1972 | Coles | |
| 4,674,204 A | 6/1987 | Sullivan et al. | |
| 4,674,205 A | 6/1987 | Anger | |
| 4,694,590 A | 9/1987 | Greenawalt | |
| 4,793,078 A | 12/1988 | Andrews | |
| 4,813,157 A | 3/1989 | Boisvert et al. | |
| 4,928,404 A | 5/1990 | Scheuermann | |
| 4,930,232 A | 6/1990 | Engle | |
| 5,154,682 A | 10/1992 | Kellerman | |
| 7,206,718 B2 * | 4/2007 | Cavanagh et al. | ........... 702/155 |
| 2006/0070260 A1 | 4/2006 | Cavanaugh et al. | |

* cited by examiner

*Primary Examiner*—John H Le
(74) *Attorney, Agent, or Firm*—McDermott Will & Emery LLP

(57) ABSTRACT

A method and apparatus is provided for generating a customized insole for footwear using information relating to pressure applied by the sole of a foot, which information is correlated to removable pieces of the insole. Embodiments include a method and apparatus for generating a customized insole for footwear, including receiving data from a pressure plate corresponding to a pressure map of the sole of a foot; determining regions of high relative pressure exceeding a predetermined relative pressure level within the pressure map; and associating data related to the regions of high relative pressure to an insole including removable insole pieces corresponding to the pressure map.

13 Claims, 9 Drawing Sheets

FIGURE 6B

METHOD AND APPARATUS FOR CUSTOMIZING INSOLES FOR FOOTWEAR

FIELD OF THE INVENTION

The present invention relates to pedorthics for preventing and relieving foot problems. The present invention has particular applicability to footwear customized for an individual.

BACKGROUND OF THE INVENTION

Foot problems and the corresponding costs associated with foot care cost millions of dollars. In cases where the foot problem is debilitating for particular activities, a number of hours of work time can be lost. Foot problems can arise from medical conditions, work conditions requiring standing or walking, athletic activities, and the like. Thus, foot problems can develop from medical conditions, work activity or leisure activity.

Pedorthics is the art concerned with the design, manufacture, fit, and modification of footwear and foot appliances as prescribed for relief of painful or disabling conditions of the foot. For those who practice any level of pedorthics, the goal is to provide protection and comfort to the consumer/patient. One of the primary ways of achieving this has been to reduce pressure at the greatest areas of impact. This has historically been accomplished with orthotics and/or external modifications to footwear.

One conventional method for providing protection and comfort to a consumer or patient is to use insoles inserted into footwear to cushion the sole of the foot. There have also been products that reduce pressure by modifying a removable insole that fits inside a shoe by removing selected pieces of the insole.

Additionally, pressure sensors that determine pressure points on the sole of the foot have been employed. However, there has never been a system which integrates digital pressure sensors and insoles with removable pieces to provide a very accurate, fast and effective way to accomplish the goal of customizing an insole for an individual.

There exists a need for an efficient method to convey information on the pressure points on the sole of a foot to customize an insole at specific pressure points for an individual.

SUMMARY OF THE INVENTION

An advantage of the present invention is a method and apparatus for generating a customized insole for footwear. The inventive method and apparatus use information relating to the pressure applied by the sole of a person's foot to customize an insole for the person by removing pieces of the insole at specific pressure points.

According to the present invention, the foregoing and other advantages are achieved in part by a method for generating a customized insole for footwear, the method comprising receiving data from a pressure plate corresponding to a pressure map of the sole of a foot, determining regions of high relative pressure exceeding a predetermined relative pressure level within the pressure map, and associating data related to the regions of high relative pressure to an insole comprising removable insole pieces corresponding to the pressure map.

Another aspect of the present invention is an apparatus comprising a pressure plate with an array of pressure sensors for generating a pressure map of the sole of a foot, and a computer-based apparatus for receiving data from the array of pressure sensors. The computer-based apparatus comprises a memory configured to store executable instructions, and one or more processors able to access the memory and configured to operate the apparatus to receive data from the pressure plate corresponding to a pressure map of the sole of a foot, determine regions of high relative pressure exceeding a predetermined relative pressure level within the pressure map, and associate data related to the regions of high relative pressure to an insole comprising removable insole pieces corresponding to the pressure map.

Additional advantages of the present invention will become readily apparent to those skilled in this art from the following detailed description, wherein only exemplary embodiments of the present invention are shown and described, simply by way of illustration of the best mode contemplated for carrying out the present invention. As will be realized, the present invention is capable of other and different embodiments, and its several details are capable of modifications in various obvious respects, all without departing from the invention. Accordingly, the drawings and description are to be regarded as illustrative in nature, and not as restrictive.

BRIEF DESCRIPTION OF THE DRAWINGS

Reference is made to the attached drawings, wherein elements having the same reference numeral designations represent like elements throughout, and wherein:

FIG. 6B is a pressure map according to an embodiment of the present invention.

DETAILED DESCRIPTION OF THE INVENTION

Figure 1:
FIG. 1 shows an exemplary pressure map obtained from a pressure sensor for use in practicing the present invention.

The present invention relates to an integrated system comprising a pressure plate capable of detecting pressure areas on the sole of a foot, and an insole with removable pieces that can be modified to account for and ease high pressure areas on the sole of the foot. The invention is usable to customize an insole for insertion into footwear to provide increased comfort, particularly for those individuals having foot problems that tend to be alleviated by relief of pressure in high pressure areas. According to the present invention, the pressure plate comprises an array of pressure sensors which detect pressure and collect data related to areas of high relative pressure. Such data is received from the pressure plate by a computer-based apparatus, and a display shows data associated with regions of high relative pressure which correspond to specific removable pieces of the insole.

An exemplary conventional pressure plate device for use in practicing the present invention is the iStep® Pressure Plate, available from Aetrex Worldwide, Inc. of Teaneck, N.J. The iStep® system for use with this pressure plate is a digital pressure analysis system that accurately takes a pressure reading of a person's feet. The technology uses pressure sensors that are 1 cm$^2$, and properly identifies which areas of a person's feet absorb the most pressure and/or impact while standing.

When using the pressure plate, a person stands on the pressure plate for 10 to 30 seconds or some other suitable amount of time, and the sensors transmit signals to a computer to map out, and illustrate, the foot. The iStep® pressure plate has 1024 sensors, but typically only about half end up in contact with the feet. In most cases, each foot encounters between 200-300 sensors, and the technology gives a reading for each sensor based on the force that is placed on the sensor, forming a "pressure map" of the foot. Like a fingerprint, this reading is always individualized, as no one has the same pressure disbursement as anyone else.

The present invention correlates the results of the pressure test with an insole for footwear and allows for pressure relief at the specific areas of the foot under the most pressure. The inventive insole is made entirely of removable pieces. In certain embodiments, the removable insole pieces are designed to correspond to the size of the sensors on the pressure plate. For example, the removable pieces are 1 cm$^2$, and so are each of the pressure plate sensors.

The practitioner of the present invention; for example, an operator in a store or in a doctor's office, determines the pressure level at which a piece of the insole should be removed. In one embodiment of the invention, the inventive software shows a color at each sensor on the pressure map, based on the pressure level. For example, the software assigns and displays 15 possible colors ranging from light blue (#1) to dark red (#15), and the operator chooses, at their discretion based on their expertise, to have the inventive software recommend removing pieces only at, say, level 14 or higher. Once this predetermined relative pressure level is set, the software identifies exactly what pieces should be removed for the particular end user.

For those who practice any level of pedorthics, the goal is to provide protection and comfort to the consumer/patient. One of the primary ways of achieving this has conventionally been to reduce pressure at the greatest areas of impact. This has historically been accomplished with orthotics and/or external modifications to footwear. There have also been examples of products that reduce pressure by modifying a removable insole that fits inside a shoe. However, there has never been a system which integrates digital pressure sensors and insoles to provide a very accurate, fast and effective way to accomplish this goal. The present invention makes it possible for any retailer or medical professional to provide this service, and therefore allows millions of consumers to receive footwear that is truly customized to their individual needs.

The invention is usable to customize a variety of types of footwear, such as therapeutic, casual or athletic footwear. It is additionally usable with other footwear styles including golf shoes, boots, sandals, and the like. In other embodiments, the inventive system is integrated with over-the-counter orthotics or insoles. In still further embodiment, the invention is used to customize a walker, also known as a fracture boot or surgical shoe, used by orthopedists, podiatrists and physical therapists post-surgery and during rehabilitation following trauma and injury of the ankle and/or foot. A walker can be used to control swelling and pain. A walker is indicated for soft tissue injuries of the foot and/or ankle, stable fractures of the ankle, midtarsal and metatarsals, as well as an adjunct to trauma and rehabilitation of the foot and ankle.

The invention is used to modify footwear to alleviate discomfort associated with foot problems, and to help treat and/or prevent many common and serious foot problems. Exemplary foot problems include diabetes related foot problems, heel pain, plantar fasciitis, Morton's neuroma, Morton's toe, metatarsalgia, heel spurs, arthritis, gout, bunions, calluses, corns, and sesamoiditis. Other exemplary foot conditions include achilles tendonitis, arch pain or strain, claw toes, hammer toes, mallet toes, neuropathy, over pronation, overlapping toes, post-tib tendonitis, and the like. These and other conditions benefit from accurately unloading pressure at the appropriate areas of the foot. Most significantly, patients with diabetes reduce the likelihood of foot ulcers by unloading pressure at the areas of their feet that are absorbing the most impact and therefore at the greatest risk for wounds.

The present invention is suitable for use in a variety of markets that sell footwear. These include shoe stores, running stores, sporting goods retailers, pharmacies, durable medical equipment stores, orthotic and prosthetic facilities, podiatry, physical therapy, Veteran's Administration or other hospital settings, outdoor retailers, and the like.

In general, the inventive customizable insole layer is placed underneath another removable insole that goes against the foot. Although the insole that is customized to an individual's feet generally does not go directly against the foot, it is understood that the customized insole can be placed directly against the foot, if desired. In addition, if the invention is used in an over-the-counter orthotic, the insole with the removable pieces also generally does not go directly against the foot. Rather, the removable pieces will generally be part of the orthotic that goes against the bottom of the shoe. Nevertheless, it is to be understood that an insole generated by the methods of the invention can be placed in any configuration, whether directly against the foot or shielded from direct contact with the foot, as desired for a particular use, as long as the footwear reflects the desired pressure relief as disclosed herein.

In one embodiment, the present invention provides a method for generating a customized insole for footwear. The method includes the steps of receiving data from a pressure plate, where the data corresponds to a pressure map of the sole of a foot; determining regions of high relative pressure exceeding a predetermined relative pressure level within the pressure map; and associating data related to the regions of high relative pressure to an insole comprising removable insole pieces corresponding to the pressure map. The pressure plate comprises an array of pressure sensors for generating a pressure map. In another embodiment, the invention provides a method for generating a customized insole for footwear. The method includes the steps of generating a pressure map of the sole of a foot; determining regions of high relative pressure exceeding a predetermined relative pressure level within the pressure map; and associating data related to the regions of high relative pressure to an insole comprising removable insole pieces corresponding to the pressure map.

As used herein, a pressure plate is a device for detecting relative pressure applied by the sole of an individual's foot. In general, such a pressure plate produces an output signal of data related to the pressure areas on the sole of a foot. As discussed above and in Example I below, the conventional iStep® pressure plate usable to practice the present invention contains an array of 1024 pressure sensors in a 32×32 grid. The sensors are composed of two separate metal components which, when connected, send a signal to a computer-related apparatus. In the istep® pressure plate, the two metal components are the iStep® footpad and a rubber mat infused with metal that is placed on top of the footpad. When an individual steps on the rubber mat, a connection is made between the mat and the footpad in areas where weight is applied where the sole of the foot contacts the mat. This connection is then used to transmit a signal to a receiving unit, such as an internal board unit, and then transmitted to a computer-based apparatus. The data received from the footpad is used to create an impression of the individual's foot and is graphically transformed to determine areas of high relative pressure; that is, to generate a pressure map. Although exemplified herein with the iStep® pressure pad, it is understood that similar types of conventional pressure plates suitable for measuring the pressure of an individual's foot can similarly be used in practicing the invention.

As used herein, a pressure map refers to a map of the sole of an individual's foot or feet relating to areas of pressure applied by the sole of the foot, in particular when an individual is standing. An example of such a pressure map is shown in FIG. 1. In the present methodology, a pressure map is used to determine areas of high relative pressure, which are used to customize an insole so that pressure is relieved at those areas of the sole of the foot exhibiting high relative pressure.

As disclosed herein, a pressure map is generated using a pressure plate and used to determine areas of high relative pressure applied by the sole of a foot. For example, in the iStep® pressure plate, each sensor detects a signal ranging from 0-255, which is converted, via software, to a relative scale of 0-15, such as with a color scheme ranging from blue to red. The higher the pressure, the redder the signal, with zeros referring to no color or no signal. Although exemplified with a relative scale of 0-15 and a color scheme, it is understood that any appropriate relative scale and increments thereof, for example, 0-20, 0-50, 0-100, and the like, or a range of colors can be used, as desired. Any scale can be used that is suitable for measuring the relative pressure, such that the data can be used in a method of the invention.

Figure 2:
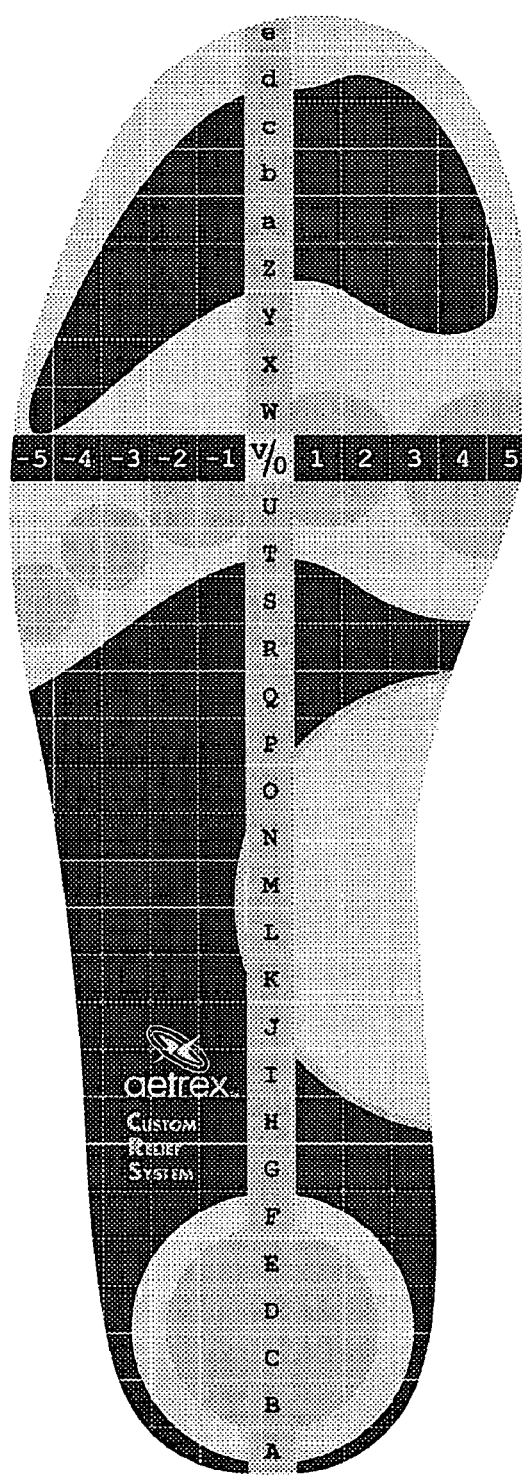
FIG. 2 shows an exemplary insole according to an embodiment of the present invention comprising a plurality of removable insole pieces.
Figure 3A:
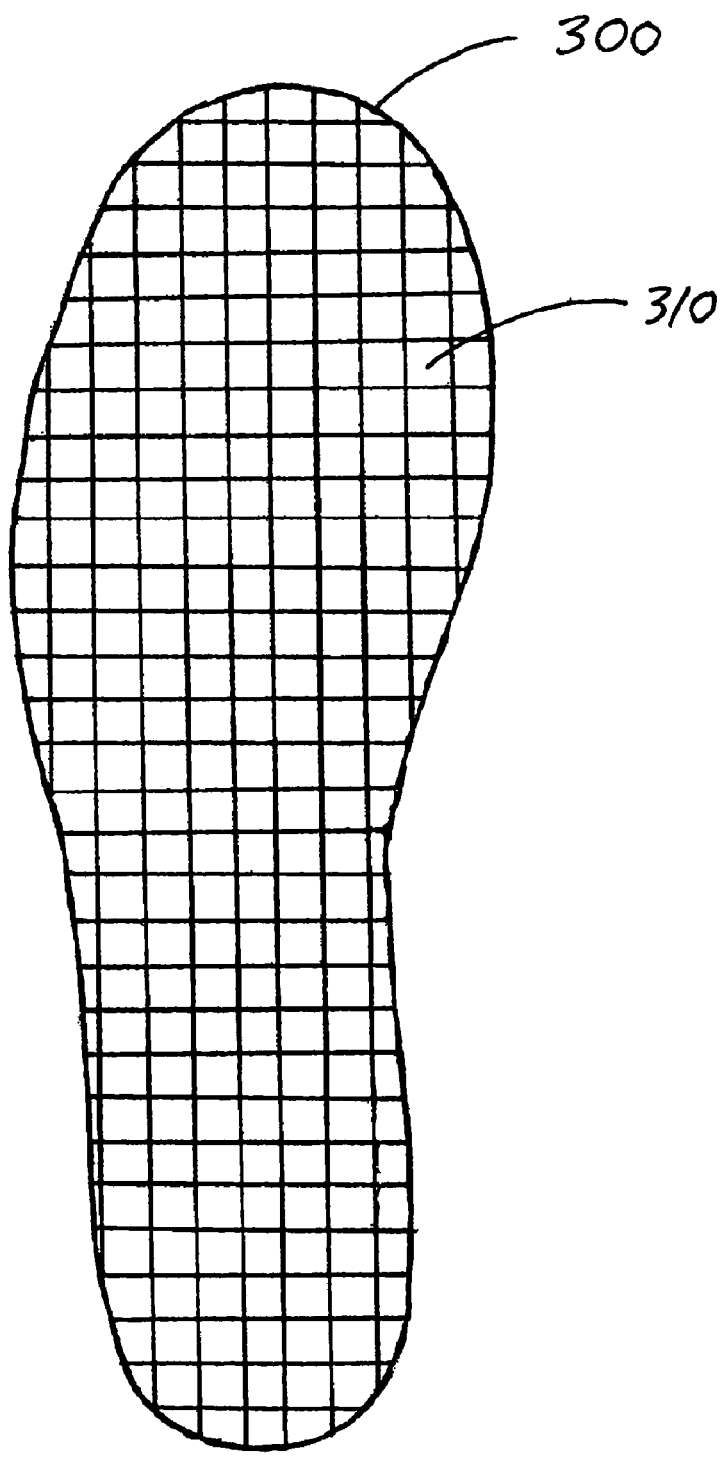
FIG. 3A shows an insole according to an embodiment of the present invention comprising a plurality of removable insole pieces.
Figure 3B:
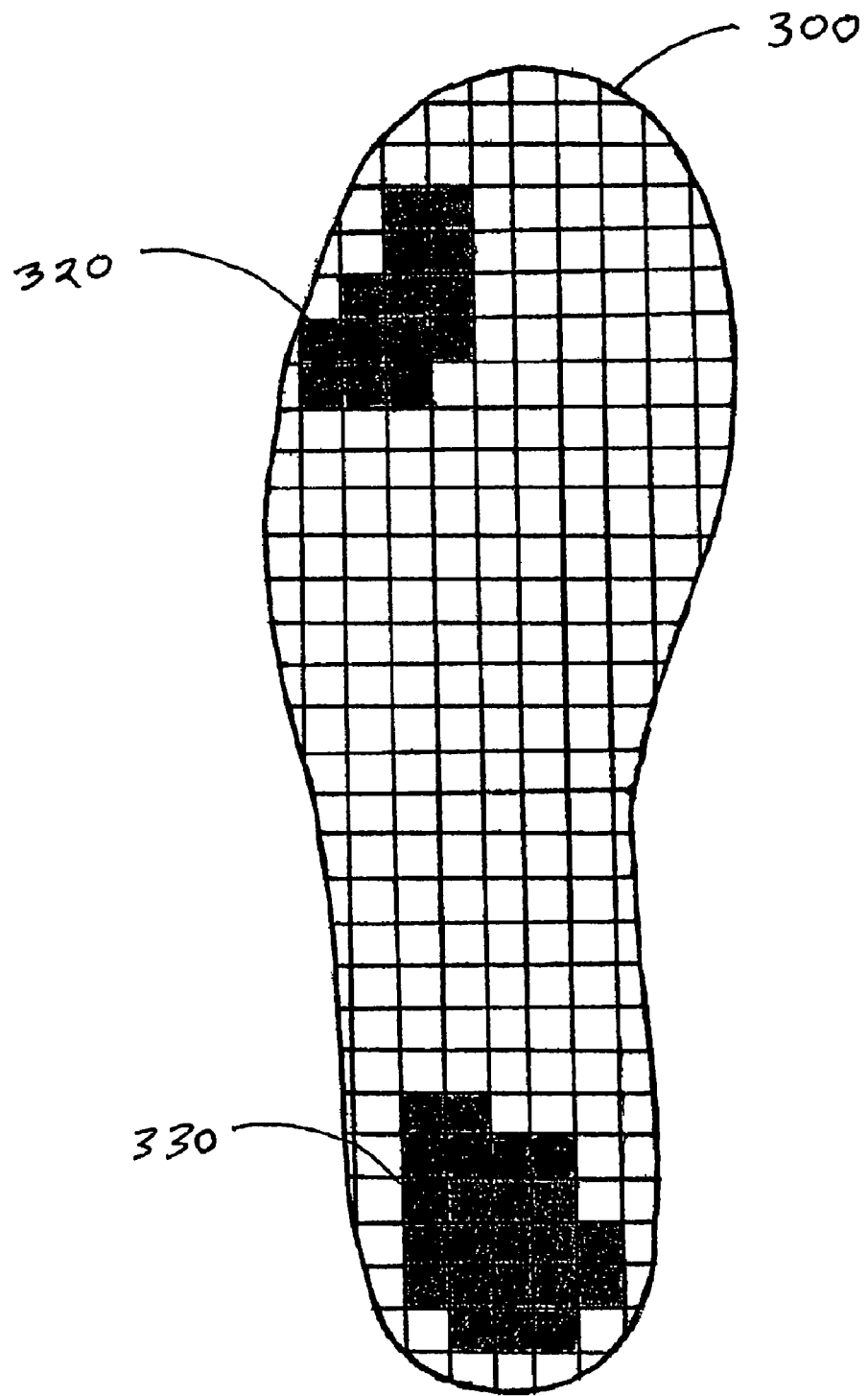
FIG. 3B shows the insole of FIG. 3A with removed pieces in specific locations associated with regions of high relative pressure.

The modifiable insole used in practicing the present invention has removable pieces; that is, pieces used to decrease the thickness of the insole in areas of high relative pressure applied by the sole of a foot. In certain embodiments, such an insole comprises a grid of removable pieces, such as illustrated in FIGS. 2, 3A and 3B. Generally, the removable pieces are of substantially similar or identical size, except for those pieces on the edge of the insole reflecting the curvature of the sole of a foot, as shown in FIG. 2. In one embodiment, the removable pieces are 1 cm$^2$, although it is understood that other sizes and shapes of removable pieces can be used, as long as it provides the ability to modify the insole to relieve areas of high relative pressure.

FIG. 3A shows insole 300 according to the present invention, comprising a plurality of removable insole pieces 310. A pressure map of the sole of a foot is used to determine regions of high relative pressure and associate data related to regions of high relative pressure to an insole comprising removable insole pieces corresponding to the pressure map. Removable insole pieces are removed from regions of high relative pressure. FIG. 3B shows insole 300 with removed pieces 320 and 330 in specific locations associated with regions of high relative pressure.

The thickness of insole 300 can vary depending on the particular use of the insole. Typically, the thickness ranges from about 3/32 of an inch to about 3/16 of an inch; for example, about 1/8 of an inch. Thus, the relief in areas of high relative pressure results from a reduced thickness of the insole in those areas of about 3/32 of an inch to about 3/16 of an inch. It is understood that other insole thicknesses can be used, as desired. In one embodiment of the present invention, the insole is composed of ethyl vinyl acetate (EVA). The insole can be made of other materials such as polyethylene or polyurethane, or other materials suitable for making an insole.

The methodology of the invention for generating a customized insole for footwear involves determining regions of high relative pressure exceeding a predetermined relative pressure level with a pressure map. As discussed above, output from a pressure plate is converted to a relative scale to identify regions of high relative pressure. In one example, the relative pressure is scaled from 0-15, where 0 relates to areas of no pressure and 15 relates to areas of the highest relative pressure. The methodology of the invention is advantageous in that a practitioner predetermines a relative pressure level above which pieces of the insole comprising a plurality of removable pieces are desired to be removed. For example, based on their experience, a practitioner determines that a pressure level of 14 or higher relates to areas of high relative pressure for which relief of high pressure by removal of removable pieces is desired to provide a customized and more comfortable insole for an individual. It is understood that this is merely exemplary and that a practitioner predetermines which relative level to associate with the desire to remove a removable piece of an insole.

The use of a predetermined relative pressure level is advantageous in that it enables a report to be generated that provides information relating to specific pieces of the insole associated with the regions of high relative pressure. The report is used to instruct the practitioner which specific removable pieces are associated with high pressure regions and are to be removed. This provides the practitioner with an accurate map of an insole and a specific indication of which insole pieces are to be removed, and a convenient output for properly and accurately modifying an insole customized to an individual's high pressure areas on the sole of a foot. Thus, a method and apparatus of the invention for generating a customized insole further includes the step of generating a report of the associated data related to the regions of high relative pressure, where the report provides information relating to specific regions of the insole associated with the regions of high relative pressure.

The report generated by the inventive apparatus and methodology can be in any desired format suitable for instructing a practitioner on which removable insole pieces to remove. For example, the report can be in the form of a list of pieces of the insole to be removed. To illustrate, the insole depicted in FIG. 2 shows a grid of letters and numbers associated with each removable insole piece, thus providing coordinates for each of the removable pieces. The report can thus be a list of which particular pieces should be removed. Similarly, such a report can be in the form of a table corresponding to a grid on the insole, where the table indicates which pieces of the insole are to be removed. In another embodiment, the report can be in the form of a map of the insole, such as illustrated in FIG. 2, with an indication of the particular pieces to be removed. It is understood that these and other suitable forms of a report can be used so long as the report conveys to the practitioner the specific removable pieces to be removed associated with regions of high relative pressure.

Thus, the report of the present invention provides information on specific regions of the insole to be modified. In some embodiments, the report provides information relating to the specific location of one or more insole pieces to be removed from the insole. An additional step of the present methodology includes removing regions of the insole corresponding to the regions of high relative pressure. In this way, a practitioner generates a customized insole for an individual that relieves pressure in areas of high relative pressure on the sole of a foot.

As discussed above, the present invention relates to using data related to regions of high relative pressure, and associating such data with an insole comprising removable insole pieces corresponding to a pressure map of the sole of a foot. Generally, such data is conveniently collected and analyzed, and a report generated using a computer-based apparatus. Any suitable combination of hardware and software can be used.

Thus, certain embodiments of the invention provide a computer-readable medium encoded with a computer program for associating data to customize an insole for footwear, which upon execution cause one or more processors to receive data from a pressure plate, the data corresponding to a pressure map of the sole of a foot; determine regions of high relative pressure exceeding a predetermined relative pressure level within the pressure map; and associate data related to the regions of high relative pressure to an insole comprising removable insole pieces corresponding to the pressure map.

The invention additionally provides a computer-based apparatus for associating data to customize an insole for footwear. The apparatus comprises a memory configured to store executable instructions, and one or more processors able to access the memory and configured to operate the apparatus to receive data from a pressure plate corresponding to a pressure map of the sole of a foot. The processor(s) determine regions of high relative pressure exceeding a predetermined relative pressure level within the pressure map, and associate data related to the regions of high relative pressure to an insole comprising removable insole pieces corresponding to the pressure map.

In yet another embodiment, the invention provides an apparatus comprising a pressure plate comprising an array of pressure sensors for generating a pressure map of the sole of a foot, and a computer-based apparatus for receiving data from the array of pressure sensors. The computer-based apparatus comprises a memory configured to store executable instructions, and one or more processors able to access the memory and configured to operate the apparatus to receive data from a pressure plate corresponding to a pressure map of the sole of a foot. The processor(s) determine regions of high relative pressure exceeding a predetermined relative pressure level within the pressure map, and associate data related to the regions of high relative pressure to an insole comprising removable insole pieces corresponding to the pressure map.

In certain embodiments, the inventive apparatus further comprises a display for showing associated data related to the regions of high relative pressure, and providing information relating to specific regions of the insole associated with the regions of high relative pressure. The display is used to convey information relating to specific regions of the insole associated with the regions of high relative pressure; that is, the display is used to communicate a report generated by a method of the invention.

Figure 4:
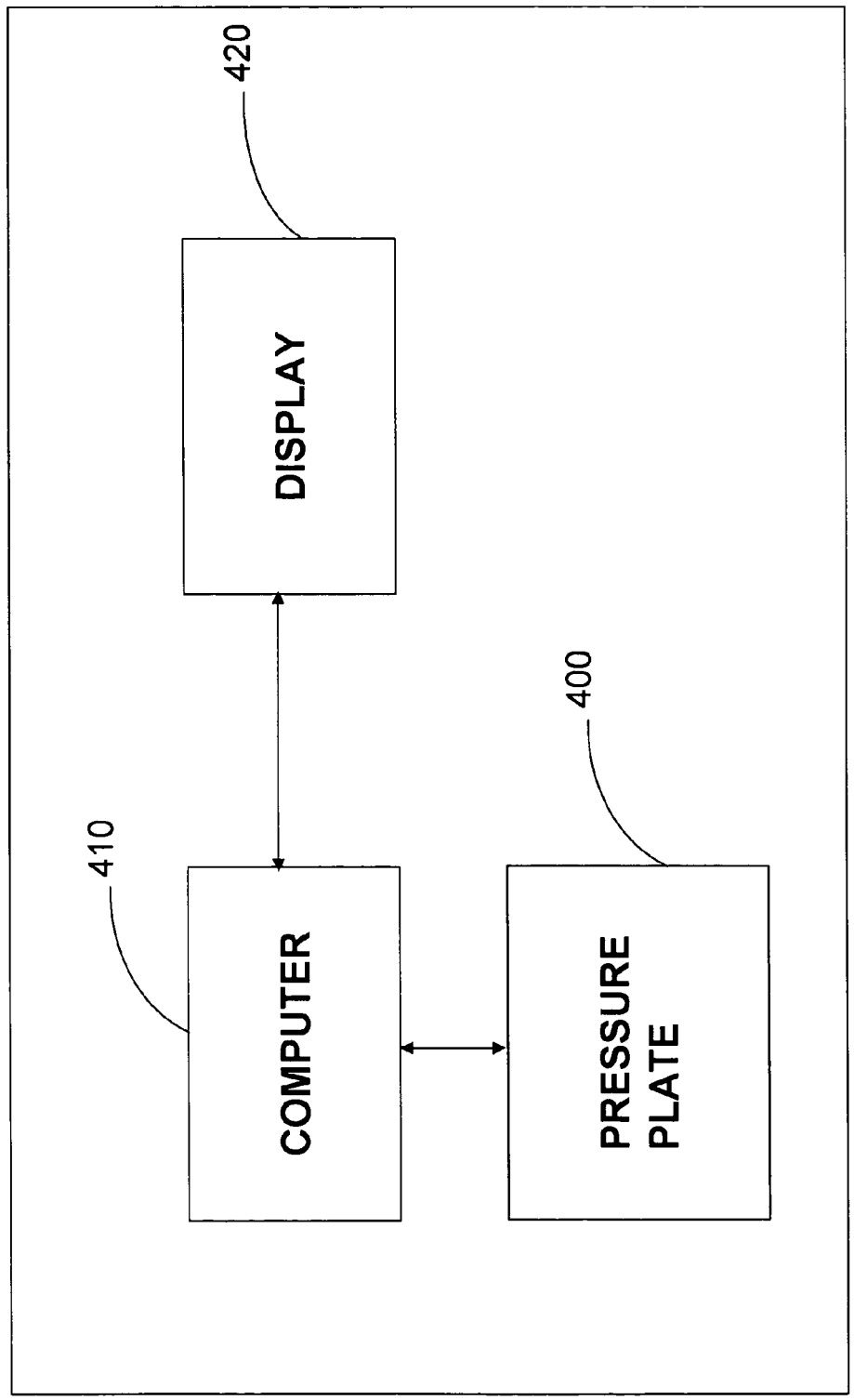
FIG. 4 is a block diagram of an apparatus according to an embodiment of the present invention.

An exemplary apparatus according to an embodiment of the present invention is depicted in FIG. 4. Pressure plate 400 comprises an array of pressure sensors which detect pressure applied by the sole of a foot, and data related to areas of high relative pressure are transmitted to and received by computer-based apparatus 410. Computer 410, such as a conventional personal computer, uses the inventive software described herein to associate data related to the regions of high relative pressure to an insole comprising removable insole pieces corresponding to the pressure map. Display 420 is for displaying data associated with regions of high relative pressure, such as a report (i.e., a list) of the high pressure regions.

As discussed above, a particular embodiment of the invention conveniently combines a pressure plate and computer-based apparatus into a single device suitable for placement in a variety of settings, including offices of medical professionals as well as retail settings. Thus, the practitioner has available a complete unit for generating a pressure map using a pressure plate, receiving data from the pressure plate, determining regions of high relative pressure and associating the data to regions of high relative pressure on an insole comprising removable insole pieces corresponding to the pressure map. However, it is understood that other configurations suitable for practicing the invention are possible. It is also understood that any suitable configuration of a pressure plate, hardware and software can be used for practicing the invention.

Certain embodiments of the invention further comprise one or more insoles comprising removable insole pieces corresponding to pressure map. Such an insole comprises a grid of removable insole pieces. In a particular embodiment of the invention, the data associated by the one or more processors is related to the specific location of one or more removable insole pieces of the insole. For example, the data associated by the one or more processors is related to the specific location of one or more removable insole pieces to be removed from the insole.

It is understood that the insoles comprise a consumable component of the invention. Thus, as one or more insoles are used to customize insoles for an individual, additional insoles will be needed for additional footwear for that individual or for other individuals. In addition, various sized insoles will be needed to accommodate various foot sizes of different individuals.

Figure 5:
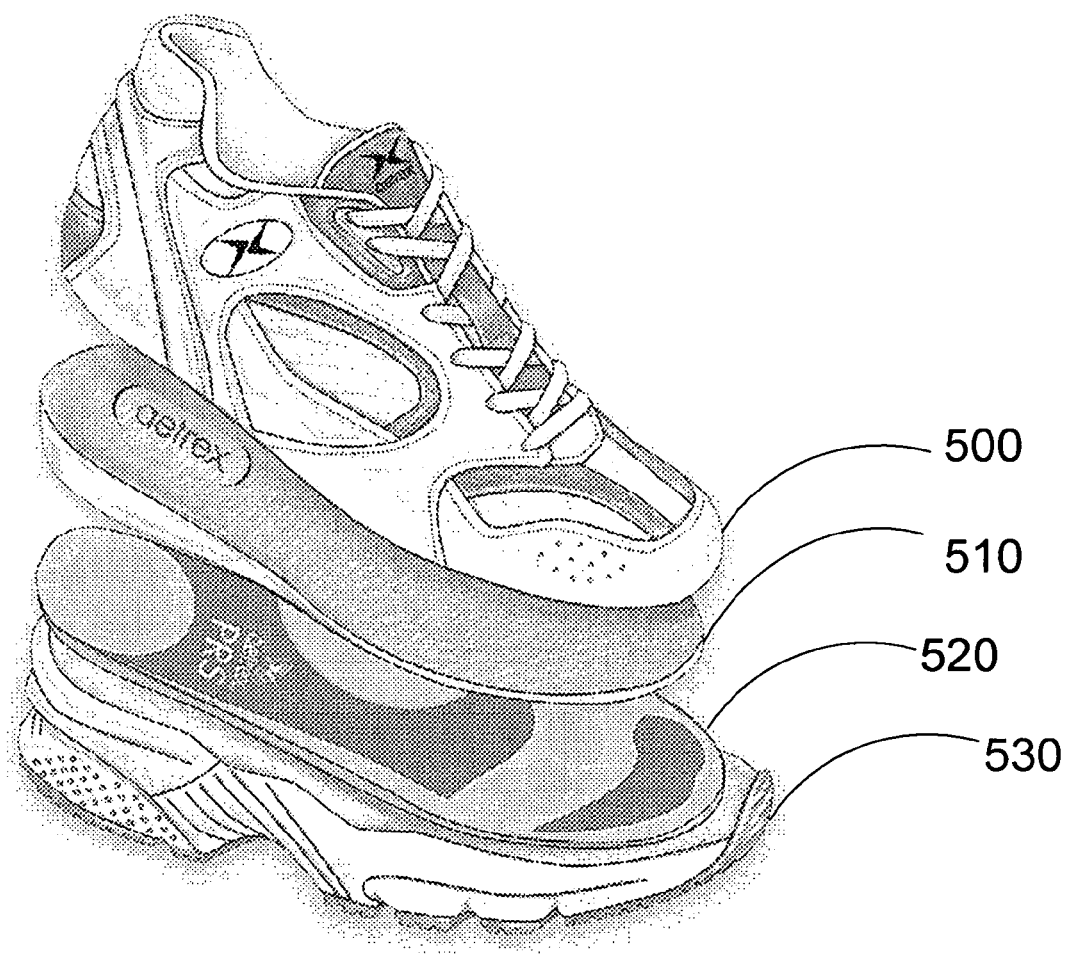
FIG. 5 shows exemplary footwear usable with an embodiment of the present invention.

As disclosed above, a customized insole generated by the inventive apparatus and methodology is used to customize various types of footwear or a walker, as desired. An example of footwear having a customized insole is shown in FIG. 5. FIG. 5 shows an expanded view of a sneaker having a customized insole. Depicted in FIG. 5 is the sneaker upper 500, an insole 510, which is positioned proximal to the foot of the wearer, an insole having removable pieces 520, and a shoe sole 530. The insole 520 having removable pieces is not shown with the grid of removable pieces but is understood to represent an insole having a grid of removable pieces as depicted in FIGS. 2, 3A and 3B. In the embodiment of FIG. 5, the insole 520 with removable pieces is not placed directly against the foot but is shielded from direct contact with the foot by insole 510.

Figure 6A:
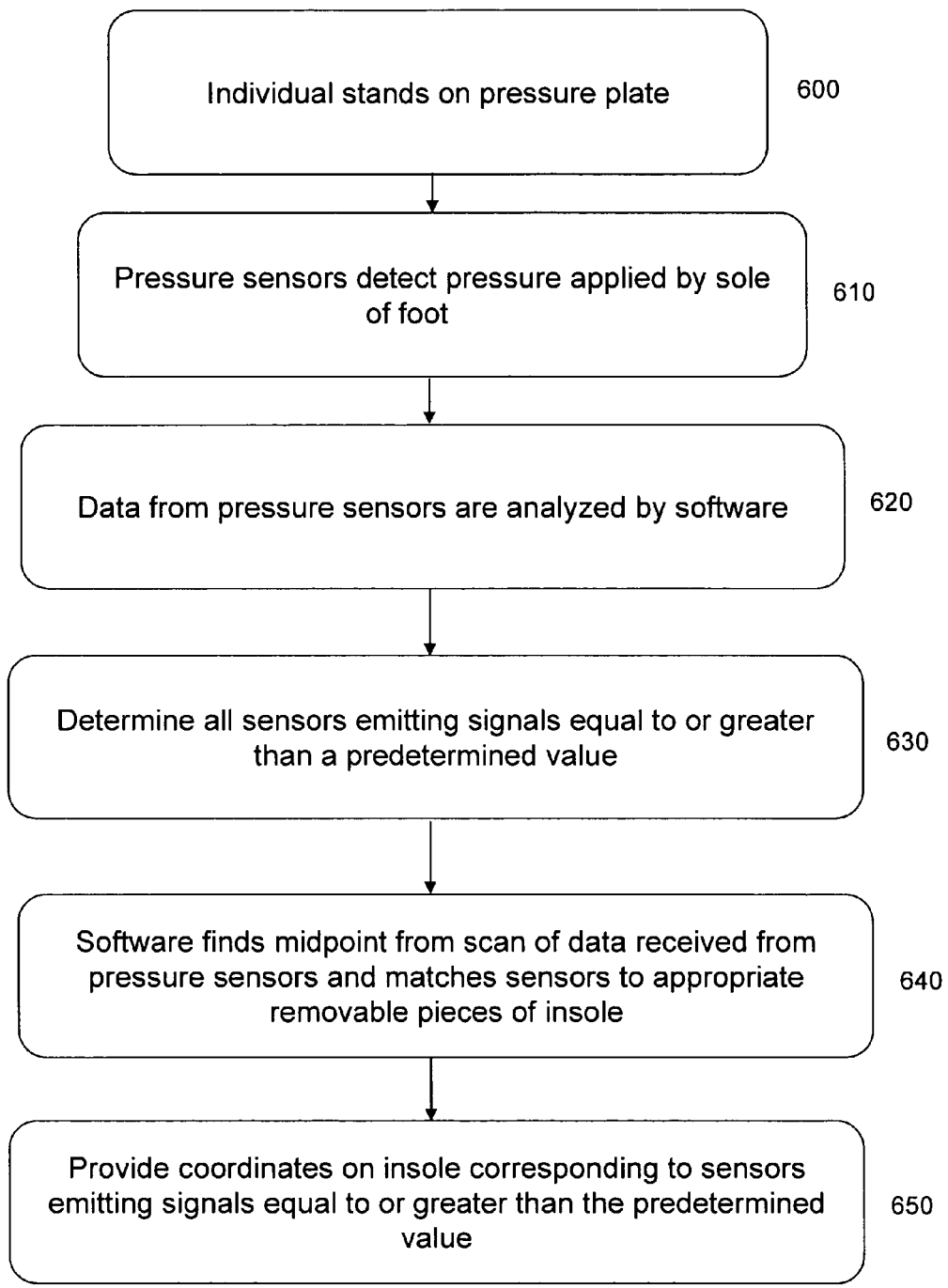
FIG. 6A shows a block diagram of software according to the present invention.

Generating a customized insole for footwear according to the inventive methodology and apparatus is exemplified in Examples I and II below, which describe generating a pressure map and customizing an insole having removable pieces for an individual. An exemplary flow diagram of an embodiment of the invention is depicted in FIG. 6A. An individual stands on a pressure plate (600), and sensors on the pressure plate detect pressure applied by the sole of a foot (610). Data from the pressure sensors are transmitted to a computer, wherein software analyzes the data (620). The software determines all sensors emitting signals equal to or greater than a predetermined value (630). The software finds the midpoint from the scan of data received from the pressure sensors, and matches sensors to appropriate removable pieces of an insole (640). The software provides coordinates on the insole having the removable pieces, corresponding to sensors emitting signals equal to or greater than the predetermined value (650). The coordinates on the insole are used to determine which pieces of the insole are to be removed corresponding to specific regions of high relative pressure (see FIG. 6C).

The following examples are intended to illustrate but not limit the present invention:

EXAMPLE I

Generating a Customized Insole for Footwear

This example describes generating a pressure map and customizing an insole for footwear.

A conventional iStep® footpad device comprises an array of 1024 sensors in a 32×32 grid. Each sensor emits a signal range from 0 to 255. The sensors are composed of 2 separate metal components which, when connected, send a signal to an internal circuit board unit. The internal board unit then sends this signal to the host computer. The host computer thus receives a frame of 1024 signal bytes from the iStep® footpad.

An individual is directed to stand on a pressure plate for about 10 to 30 seconds, or any desired amount of time suitable for the pressure plate to take an appropriate measurement, and the sensors transmit signals to the computer to map out the contacts and relative pressure of the feet on the pressure plate. Although the pressure plate has 1024 sensors, typically only about half end up in contact with the feet. Generally, each foot encounters between 200-300 sensors, and the reading for each sensor is based on the force that is placed on the sensor and is transmitted as described above. Depending on the pressure exerted on the footpad, the frame data is a series of numbers, as exemplified in Table 1.

TABLE 1

Exemplary Digital Readout from a Pressure Plate

| | | | | | | | | | | | | | | | |
|---|---|---|---|---|---|---|---|---|---|---|---|---|---|---|---|
| 0 | 0 | 0 | 0 | 0 | 0 | 0 | 0 | 0 | 0 | 0 | 0 | 0 | 0 | 0 | 0 |
| 0 | 0 | 0 | 0 | 0 | 0 | 0 | 0 | 0 | 0 | 0 | 0 | 0 | 0 | 0 | 0 |
| 0 | 0 | 0 | 0 | 0 | 0 | 0 | 0 | 0 | 0 | 0 | 0 | 0 | 0 | 0 | 0 |
| 0 | 0 | 0 | 0 | 0 | 0 | 0 | 0 | 0 | 0 | 0 | 0 | 0 | 0 | 0 | 0 |
| 0 | 0 | 0 | 0 | 0 | 0 | 0 | 0 | 0 | 0 | 0 | 0 | 0 | 0 | 0 | 0 |
| 0 | 0 | 0 | 0 | 0 | 0 | 0 | 0 | 0 | 0 | 0 | 0 | 0 | 0 | 0 | 0 |
| 0 | 0 | 0 | 0 | 0 | 0 | 0 | 0 | 0 | 0 | 0 | 0 | 0 | 0 | 0 | 0 |
| 0 | 0 | 0 | 0 | 0 | 0 | 0 | 0 | 0 | 0 | 0 | 0 | 0 | 0 | 0 | 0 |
| 0 | 0 | 0 | 0 | 0 | 0 | 0 | 0 | 0 | 0 | 0 | 0 | 0 | 0 | 0 | 0 |
| 0 | 0 | 0 | 0 | 0 | 0 | 0 | 0 | 0 | 0 | 0 | 0 | 0 | 0 | 0 | 0 |
| 0 | 0 | 0 | 0 | 0 | 0 | 0 | 0 | 0 | 0 | 0 | 0 | 0 | 0 | 0 | 0 |
| 0 | 0 | 0 | 0 | 0 | 0 | 0 | 0 | 0 | 0 | 0 | 0 | 0 | 0 | 0 | 0 |
| 0 | 0 | 0 | 0 | 0 | 0 | 0 | 0 | 0 | 0 | 0 | 0 | 0 | 0 | 0 | 0 |
| 0 | 0 | 0 | 0 | 0 | 0 | 0 | 0 | 0 | 0 | 0 | 0 | 0 | 0 | 0 | 0 |
| 0 | 0 | 0 | 0 | 0 | 0 | 0 | 12 | 0 | 17 | 13 | 0 | 0 | 0 | 0 | 0 |
| 0 | 0 | 0 | 0 | 0 | 0 | 0 | 0 | 0 | 0 | 0 | 0 | 0 | 0 | 0 | 0 |
| 0 | 0 | 0 | 0 | 0 | 0 | 0 | 11 | 23 | 37 | 24 | 0 | 0 | 0 | 0 | 0 |
| 0 | 0 | 0 | 0 | 0 | 10 | 12 | 0 | 13 | 0 | 0 | 0 | 0 | 0 | 0 | 0 |
| 0 | 0 | 0 | 0 | 11 | 0 | 0 | 0 | 14 | 32 | 37 | 0 | 0 | 0 | 0 | 0 |
| 0 | 0 | 0 | 0 | 0 | 14 | 18 | 38 | 25 | 12 | 0 | 0 | 0 | 0 | 0 | 0 |
| 0 | 0 | 0 | 0 | 0 | 0 | 18 | 19 | 24 | 36 | 2 | 0 | 0 | 0 | 0 | 0 |
| 0 | 0 | 0 | 0 | 0 | 0 | 17 | 55 | 43 | 19 | 0 | 0 | 0 | 0 | 0 | 0 |
| 0 | 0 | 0 | 0 | 12 | 23 | 35 | 52 | 68 | 73 | 56 | 18 | 0 | 0 | 0 | 0 |
| 0 | 0 | 0 | 0 | 0 | 15 | 33 | 57 | 32 | 16 | 0 | 0 | 0 | 0 | 0 | 0 |
| 0 | 0 | 0 | 11 | 33 | 58 | 79 | 86 | 115 | 163 | 127 | 34 | 0 | 0 | 0 | 0 |
| 0 | 0 | 0 | 0 | 19 | 22 | 52 | 77 | 54 | 29 | 0 | 0 | 0 | 0 | 0 | 0 |
| 0 | 0 | 27 | 45 | 54 | 73 | 78 | 101 | 164 | 245 | 210 | 52 | 0 | 0 | 0 | 0 |
| 0 | 0 | 0 | 0 | 14 | 37 | 78 | 82 | 60 | 24 | 0 | 0 | 0 | 0 | 0 | 0 |
| 0 | 11 | 53 | 72 | 77 | 77 | 79 | 93 | 156 | 248 | 212 | 35 | 0 | 0 | 0 | 0 |
| 0 | 0 | 0 | 0 | 16 | 39 | 73 | 95 | 52 | 37 | 18 | 12 | 0 | 0 | 0 | 0 |
| 0 | 25 | 84 | 99 | 73 | 65 | 68 | 72 | 119 | 133 | 71 | 0 | 0 | 0 | 0 | 0 |
| 0 | 0 | 0 | 0 | 0 | 12 | 41 | 56 | 48 | 23 | 27 | 21 | 14 | 0 | 0 | 0 |
| 0 | 21 | 88 | 93 | 67 | 53 | 49 | 55 | 58 | 32 | 17 | 0 | 0 | 0 | 0 | 0 |
| 0 | 0 | 0 | 0 | 0 | 0 | 23 | 35 | 34 | 28 | 24 | 23 | 17 | 11 | 0 | 0 |
| 0 | 14 | 61 | 85 | 54 | 48 | 33 | 37 | 22 | 27 | 0 | 0 | 0 | 0 | 0 | 0 |
| 0 | 0 | 0 | 0 | 0 | 0 | 13 | 29 | 22 | 13 | 26 | 12 | 18 | 0 | 0 | 0 |
| 0 | 14 | 37 | 62 | 53 | 47 | 32 | 26 | 21 | 18 | 0 | 0 | 0 | 0 | 0 | 0 |
| 0 | 0 | 0 | 0 | 0 | 0 | 0 | 13 | 17 | 11 | 16 | 19 | 12 | 0 | 0 | 0 |
| 0 | 0 | 34 | 67 | 53 | 49 | 32 | 15 | 18 | 0 | 0 | 0 | 0 | 0 | 0 | 0 |
| 0 | 0 | 0 | 0 | 0 | 0 | 0 | 0 | 0 | 0 | 11 | 14 | 12 | 0 | 0 | 0 |
| 0 | 0 | 39 | 62 | 58 | 42 | 37 | 16 | 0 | 0 | 0 | 0 | 0 | 0 | 0 | 0 |
| 0 | 0 | 0 | 0 | 0 | 0 | 0 | 0 | 0 | 0 | 18 | 14 | 15 | 0 | 0 | 0 |
| 0 | 0 | 22 | 57 | 52 | 34 | 28 | 11 | 0 | 0 | 0 | 0 | 0 | 0 | 0 | 0 |
| 0 | 0 | 0 | 0 | 0 | 0 | 0 | 0 | 0 | 0 | 13 | 15 | 12 | 0 | 0 | 0 |
| 0 | 0 | 17 | 37 | 44 | 36 | 22 | 18 | 0 | 0 | 0 | 0 | 0 | 0 | 0 | 0 |
| 0 | 0 | 0 | 0 | 0 | 0 | 0 | 0 | 0 | 0 | 17 | 13 | 0 | 0 | 0 | 0 |
| 0 | 0 | 14 | 27 | 33 | 39 | 36 | 31 | 0 | 0 | 0 | 0 | 0 | 0 | 0 | 0 |
| 0 | 0 | 0 | 0 | 0 | 0 | 0 | 0 | 0 | 0 | 10 | 0 | 0 | 0 | 0 | 0 |
| 0 | 0 | 0 | 27 | 40 | 52 | 75 | 71 | 39 | 0 | 0 | 0 | 0 | 0 | 0 | 0 |
| 0 | 0 | 0 | 0 | 0 | 0 | 12 | 28 | 11 | 19 | 0 | 0 | 0 | 0 | 0 | 0 |
| 0 | 0 | 0 | 23 | 47 | 92 | 120 | 111 | 66 | 0 | 0 | 0 | 0 | 0 | 0 | 0 |
| 0 | 0 | 0 | 0 | 0 | 17 | 52 | 64 | 59 | 12 | 0 | 0 | 0 | 0 | 0 | 0 |
| 0 | 0 | 0 | 14 | 62 | 147 | 177 | 140 | 94 | 0 | 0 | 0 | 0 | 0 | 0 | 0 |
| 0 | 0 | 0 | 0 | 0 | 49 | 95 | 111 | 96 | 43 | 0 | 0 | 0 | 0 | 0 | 0 |
| 0 | 0 | 0 | 18 | 72 | 166 | 189 | 173 | 100 | 11 | 0 | 0 | 0 | 0 | 0 | 0 |
| 0 | 0 | 0 | 0 | 0 | 74 | 138 | 153 | 127 | 63 | 15 | 0 | 0 | 0 | 0 | 0 |
| 0 | 0 | 0 | 12 | 68 | 141 | 205 | 164 | 108 | 19 | 0 | 0 | 0 | 0 | 0 | 0 |

TABLE 1-continued

Exemplary Digital Readout from a Pressure Plate

| 0 | 0 | 0 | 0 | 0  | 77  | 142 | 147 | 121 | 65  | 0 | 0 | 0 | 0 | 0 | 0 |
|---|---|---|---|----|-----|-----|-----|-----|-----|---|---|---|---|---|---|
| 0 | 0 | 0 | 0 | 28 | 109 | 150 | 132 | 57  | 0   | 0 | 0 | 0 | 0 | 0 | 0 |
| 0 | 0 | 0 | 0 | 0  | 42  | 113 | 131 | 108 | 23  | 0 | 0 | 0 | 0 | 0 | 0 |
| 0 | 0 | 0 | 0 | 0  | 16  | 39  | 32  | 0   | 0   | 0 | 0 | 0 | 0 | 0 | 0 |
| 0 | 0 | 0 | 0 | 0  | 0   | 21  | 0   | 0   | 0   | 0 | 0 | 0 | 0 | 0 | 0 |

The signal range from 0 to 255 is converted to a color scheme ranging from blue to red. The higher the number, the redder or hotter the converted color. Zeros (0) are converted to no color or no signal, meaning that there is no pressure being exerted on that sensor. When graphically transformed, the signals create the impression of the individual's foot or feet. At the same time, when the data is graphically transformed, the relative higher pressured areas are identified.

The data is converted into a pressure map that is interfaced with an insole comprising removable insole pieces. The pressure map indicates the pressure applied by the sole of a foot and the regions of high relative pressure. An insole comprising removable insole pieces corresponds to the pressure map. An example of such an insole with removable insole pieces in the form of a grid is shown in FIGS. 2, 3A and 3B. Since the removable insole pieces correspond to the pressure map, the information from the pressure map on areas of high relative pressure are used to determine specific removable insole pieces corresponding to regions of high relative pressure. The practitioner predetermines a relative pressure level above which indicates a desire to remove particular removable insole pieces, for example a level of 14 or above on a scale of 15. The predetermined relative pressure level is programmed into the software handling the data from the pressure plate. The computer's display shows the data associated with regions of high relative pressure. The display provides a report on the specific removable insole pieces on the grid of the insole that correspond to the regions of high relative pressure above the predetermined relative pressure level. Such a report provides directions to a practitioner as to which of the removable pieces of the insole are to be removed to customize the insole with respect to the high pressure areas for an individual. FIG. 3B shows an example of an insole 300 from which removable insole pieces corresponding to regions of high relative pressure have been removed.

EXAMPLE II

Generating a Customized Insole for Footwear

This example describes customizing footwear for an individual.

An exemplary scheme for generating a pressure map to customize an insole to an individual is shown in FIG. 6A. To generate a customized insole, an individual stands on a pressure plate (step 600), such as an iStep® pressure plate, for an appropriate amount of time to determine the pressure points on the sole of each foot, for example 10 to 30 seconds. As discussed in Example I, the iStep® footpad is a pressure plate containing an array of 1024 sensors in a 32×32 grid. The pressure sensors detect pressure applied by the sole of a foot (step 610). On those sensors on which pressure is detected, a signal is generated and transmitted to a computer. Data from the pressure sensors are analyzed by software (step 620).

Figure 6B:
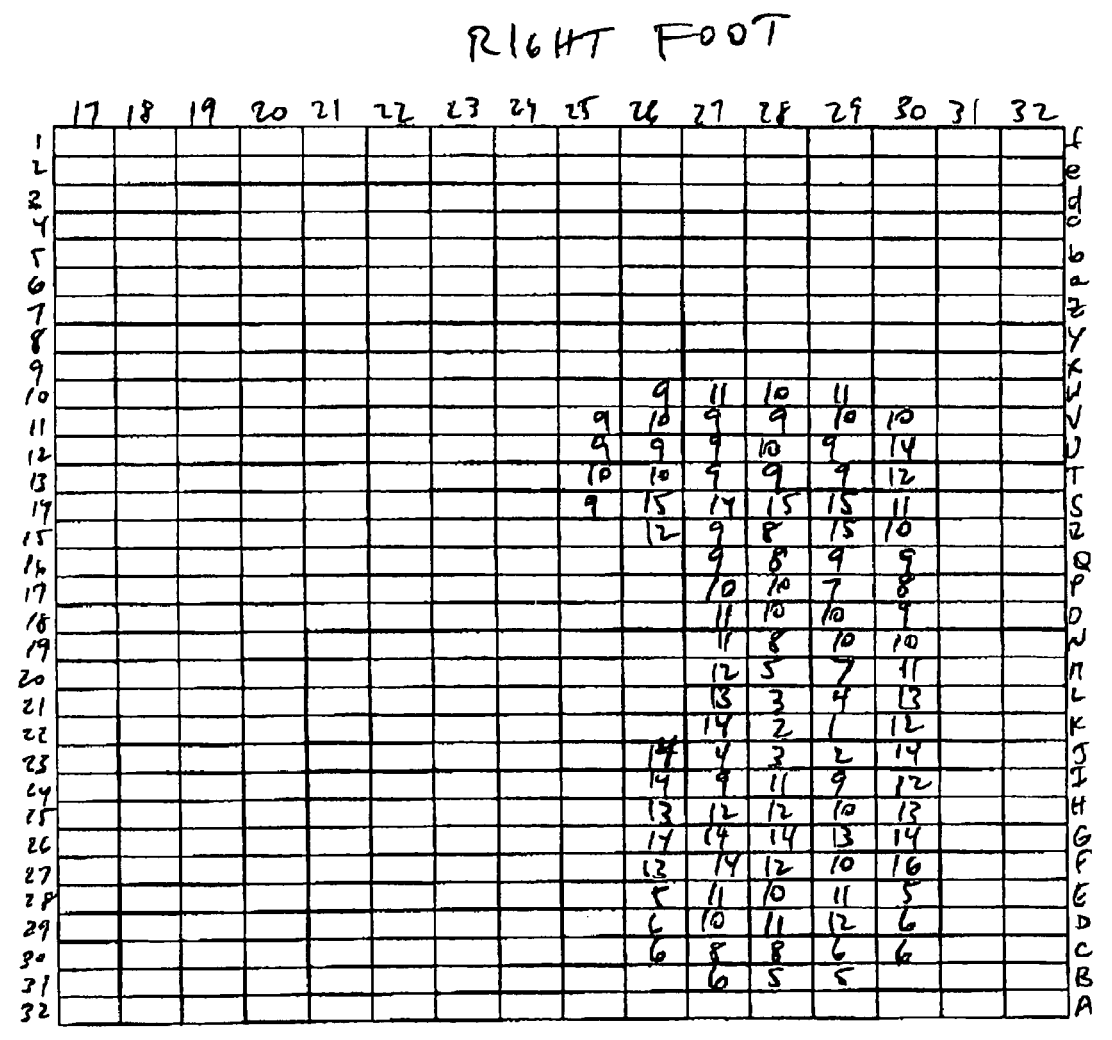

The data output received by the software is converted to a scale, for example, a scale of 0 to 15 and/or a color scale. FIG. 6B shows an exemplary pressure map on a 32×32 grid, with data on a scale of 0 to 15 (zeroes not shown) for those sensors detecting pressure applied by the sole of a right foot. The software determines all sensors emitting signals equal to or greater than a predetermined value (step 630). In one example, the practitioner determines that a level of 14 or higher on the scale of 0 to 15 corresponds to a region of high relative pressure at which it is desired to remove a piece of an insole to relieve pressure at that specific site.

The software uses the data to determine the midpoint from the scan of pressure readings (step 640). In FIG. 6B, the midpoint is in column 28. The software also matches sensors to appropriate removable pieces of an insole, such as that shown in FIGS. 2 and 3A, having removable pieces that correspond to a grid on the pressure map.

Figure 6C:
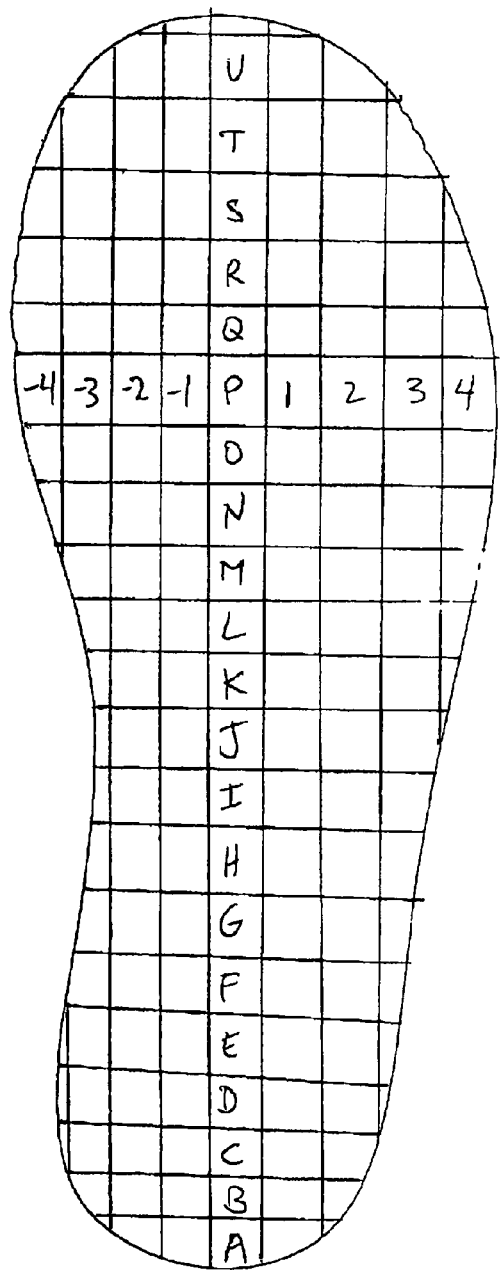
FIG. 6C is a display of a result of the software of FIG. 6A.

At those sensors emitting signals equal to or greater than the predetermined value, the software provides an output of information on the coordinates on the insole having removable pieces (step 650). Thus, in those areas of the pressure map having a signal equal to or above the predetermined value, information is provided on the specific removable pieces on the insole that correspond to the regions of high relative pressure. These coordinates correspond to specific pieces on the insole to be removed. An example of such an insole is shown in FIG. 6C, along with a list of coordinates of pieces to be removed as generated in step 650 of FIG. 6A. As shown in FIG. 6C, based on the coordinates determined on the pressure map of FIG. 6B, removable pieces S0, −S1, −S2, S1 and R1 are removed to provide a customized insole corresponding to the pressure map of FIG. 6B. The customized insole is placed into footwear or a walker, as desired.

The present invention can be practiced by employing conventional materials, methodology and equipment. Accordingly, the details of such materials, equipment and methodology are not set forth herein in detail. In the previous descriptions, numerous specific details are set forth, such as specific materials, structures, processes, etc., in order to provide a thorough understanding of the present invention. However, it should be recognized that the present invention can be practiced without resorting to the details specifically set forth. In other instances, well known processing structures have not been described in detail, in order not to unnecessarily obscure the present invention.

Only exemplary embodiments of the present invention and but a few examples of its versatility are shown and described in the present disclosure. It is to be understood that the present invention is capable of use in various other combinations and environments and is capable of changes or modifications within the scope of the inventive concept as expressed herein.

What is claimed is:

1. A method for customizing an insole for footwear, the method comprising:
   (a) receiving data from a pressure plate, said data corresponding to a two-dimensional pressure map of the sole of a foot;

(b) determining regions of high relative pressure exceeding a predetermined relative pressure level within said pressure map;
(c) associating data related to the regions of high relative pressure to a pre-manufactured insole comprising removable insole pieces, wherein said pre-manufactured insole corresponds to the size of said foot; and
(d) manually removing said insole pieces corresponding to said pressure map.

2. The method of claim 1, wherein said pressure plate comprises an array of pressure sensors for generating said pressure map.

3. The method of claim 1, further comprising generating a report of the associated data related to the regions of high relative pressure, wherein the report provides information relating to said removable pieces of said insole associated with the regions of high relative pressure.

4. The method of claim 3, wherein the report provides information on specific regions of said insole to be manually removed.

5. The method of claim 1, wherein said insole comprises one or more removable insole pieces.

6. The method of claim 3, wherein the report provides information on the specific location of one or more insole pieces to be removed from said insole.

7. The method of claim 6, further comprising customizing said insole by removing regions of said insole corresponding to the regions of high relative pressure.

8. An apparatus comprising:
a pressure plate having an array of pressure sensors for generating a two-dimensional pressure map of the sole of a foot; and
a computer-readable medium encoded with a computer program for associating data to customize a pre-manufactured insole for footwear by manually removing removable insole pieces from said insole, which upon execution cause one or more processors to:
(a) receive data from a pressure plate, said data corresponding to said pressure map of the sole of said foot;
(b) determine regions of high relative pressure exceeding a predetermined relative pressure level within said pressure map; and
(c) associate data related to the regions of high relative pressure to said insole comprising removable insole pieces corresponding to said pressure map such that said insole can be customized by removing said pieces.

9. The apparatus of claim 8, further comprising a display showing the associated data related to the regions of high relative pressure, wherein the display provides information relating to specific regions of said insole associated with the regions of high relative pressure.

10. The apparatus of claim 8, further comprising one or more insoles comprising removable insole pieces corresponding to said pressure map.

11. The apparatus of claim 8, wherein said insole comprises one or more removable insole pieces.

12. The apparatus of claim 8, wherein the data associated by said one or more processors is related to the specific location of one or more removable insole pieces.

13. The apparatus of claim 8, wherein the data associated by said one or more processors is related to the specific location of one or more removable insole pieces to be removed from said insole.

* * * * *

UNITED STATES PATENT AND TRADEMARK OFFICE
CERTIFICATE OF CORRECTION

| | | |
|---|---|---|
| PATENT NO. | : 7,493,230 B2 | Page 1 of 1 |
| APPLICATION NO. | : 11/447305 | |
| DATED | : February 17, 2009 | |
| INVENTOR(S) | : Evan Schwartz et al. | |

It is certified that error appears in the above-identified patent and that said Letters Patent is hereby corrected as shown below:

On the title page, in Item "(56) References Cited", insert the following:

-- OTHER PUBLICATIONS

International Search Report and Written Opinion of the
International Searching Authority, issued in
International Application No. PCT/US07/13168, mailed
July 18, 2008 --

Signed and Sealed this

Sixteenth Day of March, 2010

David J. Kappos
*Director of the United States Patent and Trademark Office*